(12) United States Patent
Park et al.

(10) Patent No.: US 10,295,519 B2
(45) Date of Patent: May 21, 2019

(54) WATER QUALITY SENSOR USING POSITIVE FEEDBACK

(71) Applicants: Seoul National University R&DB Foundation, Seoul (KR); Seoul Viosys Co., Ltd., Ansan-si, Gyeonggi-do (KR)

(72) Inventors: Young June Park, Seoul (KR); Seong Wook Choi, Seoul (KR); Sang Woo Lee, Seoul (KR)

(73) Assignees: SEOUL NATIONAL UNIVERSITY R&DB FOUNDATION, Seoul (KR); SEOUL VIOSYS CO., LTD., Ansan-si, Gyeonggi-Do (KR)

( * ) Notice: Subject to any disclaimer, the term of this patent is extended or adjusted under 35 U.S.C. 154(b) by 259 days.

(21) Appl. No.: 15/026,506

(22) PCT Filed: Oct. 28, 2014

(86) PCT No.: PCT/KR2014/010208
§ 371 (c)(1),
(2) Date: Mar. 31, 2016

(87) PCT Pub. No.: WO2015/065023
PCT Pub. Date: May 7, 2015

(65) Prior Publication Data
US 2016/0238581 A1    Aug. 18, 2016

(30) Foreign Application Priority Data
Oct. 29, 2013  (KR) .................. 10-2013-0129131
Jul. 17, 2014  (KR) .................. 10-2014-0090256

(51) Int. Cl.
*H01L 31/14* (2006.01)
*G01N 33/18* (2006.01)
(Continued)

(52) U.S. Cl.
CPC ............. *G01N 33/18* (2013.01); *G01N 15/06* (2013.01); *G01N 21/33* (2013.01); *G01N 21/534* (2013.01); *G01N 2015/0693* (2013.01)

(58) Field of Classification Search
CPC ................................ G01N 15/06; G01N 33/18
(Continued)

(56) References Cited

U.S. PATENT DOCUMENTS 3,437,822 A     4/1969   Fitzsimmons
4,077,724 A  *  3/1978   Briggs ................... G01N 21/85
                                                              250/564
(Continued)

FOREIGN PATENT DOCUMENTS

CN       1473021 A    2/2004
CN     102901992 A    1/2013
(Continued)

OTHER PUBLICATIONS

Chinese Office Action for related CN Application No. 201480059243.0 dated Dec. 13, 2017 from Chinese Patent Office.
(Continued)

*Primary Examiner* — Thanh Luu
*Assistant Examiner* — Kevin Wyatt
(74) *Attorney, Agent, or Firm* — Paratus Law Group, PLLC (57) ABSTRACT

A sensing system according to the embodiment of the present invention includes an optical actuator configured to apply an optical stimulus into a detection target substance, a photo detector configured to output an electrical signal having a snapback form in response to an optical response generated according to a concentration of the detection target substance to which the optical stimulus is applied, an amplifier configured to amplify the electrical signal output from the photo detector and to provide the amplified elec-
(Continued)

trical signal as positive feedback to the optical actuator, and a detection unit configured to detect the detection target substance in response to the electrical signal.

18 Claims, 11 Drawing Sheets

(51) Int. Cl.
 *G01N 15/06* (2006.01)
 *G01N 21/33* (2006.01)
 *G01N 21/53* (2006.01)
(58) Field of Classification Search
 USPC .......................................................... 250/564
 See application file for complete search history.

(56) References Cited

U.S. PATENT DOCUMENTS

| | | |
|---|---|---|
| 4,264,830 A | 4/1981 | Maurer et al. |
| 4,270,046 A | 5/1981 | Werking |
| 7,090,992 B2 | 8/2006 | Simpson et al. |
| 9,816,858 B2* | 11/2017 | Choi .......................... G01J 1/44 |
| 2004/0012783 A1 | 1/2004 | Morokawa et al. |
| 2013/0026350 A1 | 1/2013 | Yao et al. |
| 2014/0342467 A1* | 11/2014 | Kim ................... G01N 33/1813 |
| | | 436/501 |

FOREIGN PATENT DOCUMENTS

| | | |
|---|---|---|
| KR | 10-2006-0124111 A | 12/2006 |
| KR | 10-2009-0081705 A | 7/2009 |
| KR | 10-1004450 B1 | 12/2010 |
| WO | WO 2010-090391 A2 | 8/2010 |
| WO | WO 2013/032138 A2 | 3/2013 |
| WO | WO 2013-032138 A2 | 3/2013 |

OTHER PUBLICATIONS

Chinese Office Action for related CN Application No. 201480059243.0 dated Aug. 10, 2018 from Chinese Patent Office.

* cited by examiner

WATER QUALITY SENSOR USING POSITIVE FEEDBACK

CROSS REFERENCE TO PRIOR APPLICATION

This application is a National Stage Patent Application of PCT International Patent Application No. PCT/KR2014/010208 (filed on Oct. 28, 2014) under 35 U.S.C. § 371, which claims priority to Korean Patent Application Nos. 10-2013-0129131 (filed on Oct. 29, 2013) and 10-2014-0090256 (filed on Jul. 17, 2014), which are all hereby incorporated by reference in their entirety.

TECHNICAL FIELD

The present invention relates to a water quality sensor using positive feedback.

BACKGROUND ART

A conventional water quality sensing system using an actuator and a sensor constantly maintains the magnitude of an input signal generated in the actuator to detect the change of a medium formed by the actuator. A sensing system according to the prior art uses single ended signal scheme and/or a negative feedback configuration for a more stable structure.

For example, when an actuator irradiates a medium containing a substance of which a concentration to be measured with a certain amount of light, a turbidity sensor detects and converts the light transmitted through the medium into an electrical signal to measure the concentration of the substance in the medium.

DISCLOSURE

Technical Problem

An existing sensing system has a limit of detection (LOD). For example, when the sensing system is used as a water quality sensor, even if a very small amount of material to be detected is included, that is, the amount of included material is less than the LOD, it is determined that the material is not included because the LOD characteristic of the sensing system is poor.

The present invention is to address the above described problem of the conventional sensing system according to the prior art, so that one object of the present invention is to provide a sensing system of a superior LOD characteristic capable of detecting a trace amount of a substance, with high sensitivity.

Technical Solution

A sensing system according to the embodiment of the present invention includes an optical actuator configured to apply an optical stimulus into a detection target substance, a photo detector configured to output an electrical signal having a snapback form in response to an optical response generated according to a concentration of the detection target substance to which the optical stimulus is applied, an amplifier configured to amplify the electrical signal output from the photo detector and to provide the amplified electrical signal as positive feedback to the optical actuator, and a detection unit configured to detect the detection target substance in response to the electrical signal.

Advantageous Effects

A sensing system according to an embodiment of the present invention provides an advantage of detecting a trace amount of a detection target substance, which is very difficult to be detected by a conventional sensor.

MODES OF THE INVENTION

Since a description of the present invention is only intended for structural and functional description of the embodiments, the scope of the present invention is not to be construed as being limited by the embodiments described herein. That is, because the various embodiments may vary and can have many different forms, the scope of the present invention should be understood to include equivalents for realizing the technical concept.

Meanwhile, the meanings of terms described herein should be understood as follows.

As described herein, expression in the singular should be understood to include a plural meaning, unless there is a clearly different meaning in the context, and the terms of "comprise" and/or "include" and the like specify the presence of stated features, numbers, steps, operations, elements, parts, and/or a combination thereof, but do not preclude the presence or addition of one or more other features, numbers, steps, operations, elements, parts, and/or a combination thereof.

In the accompanying drawings illustrating the embodiments of the present disclosure, the size, height, thickness and the like of a component may be exaggerated by design for ease of understanding and convenience of description, and may not be expanded or reduced according to a ratio. It will be further understood that one component illustrated in the drawing may be reduced by design, or another component therein may be expanded by design.

Unless otherwise defined, all terms used herein have the same meaning as commonly understood by those skilled in the art to which the invention pertains. General terms that are defined in a dictionary shall be construed to have meanings that are consistent in the context of the relevant art, and will not be interpreted as having an idealistic or excessively formalistic meaning unless clearly defined in the present application.

Figure 1:
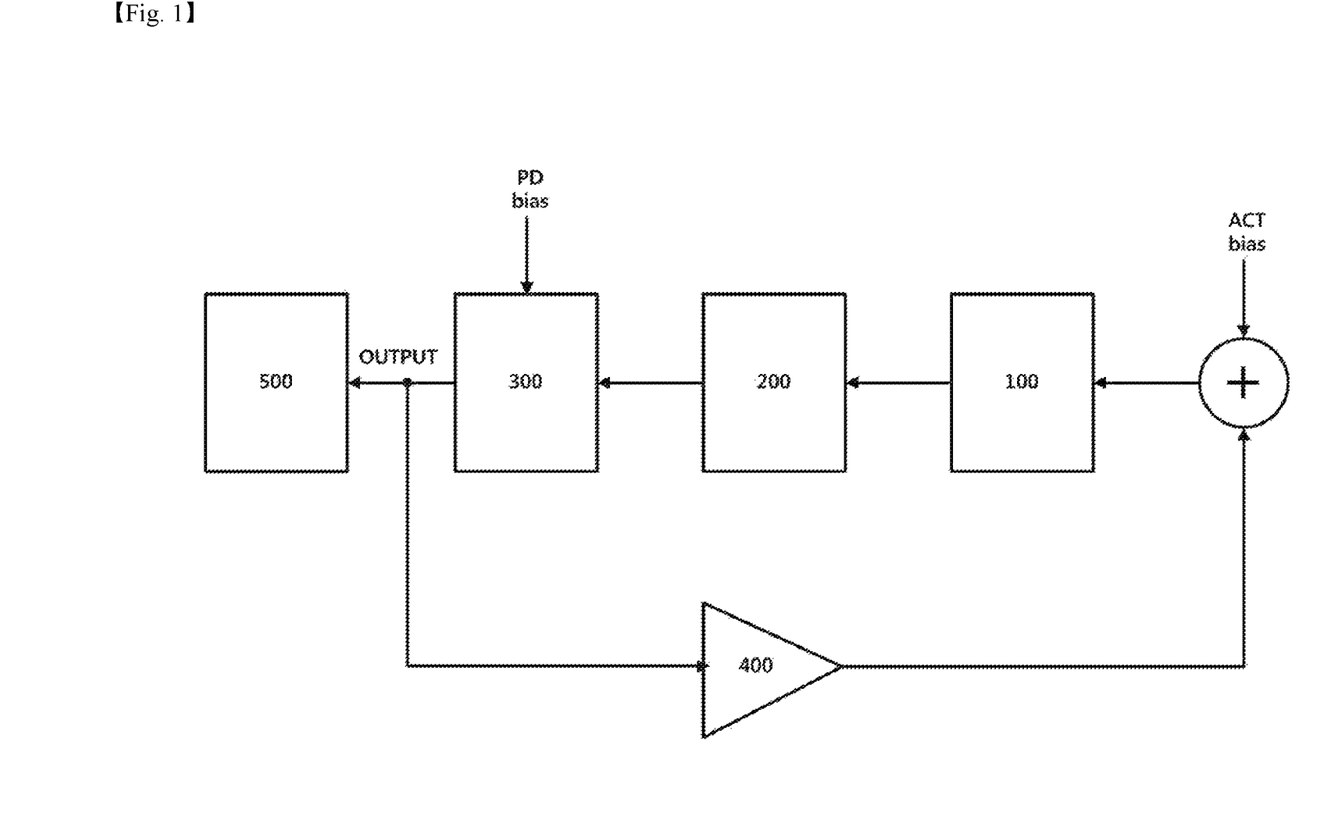
FIG. 1 illustrates a block diagram showing a sensing system according to an embodiment of the present invention.
Figure 2:
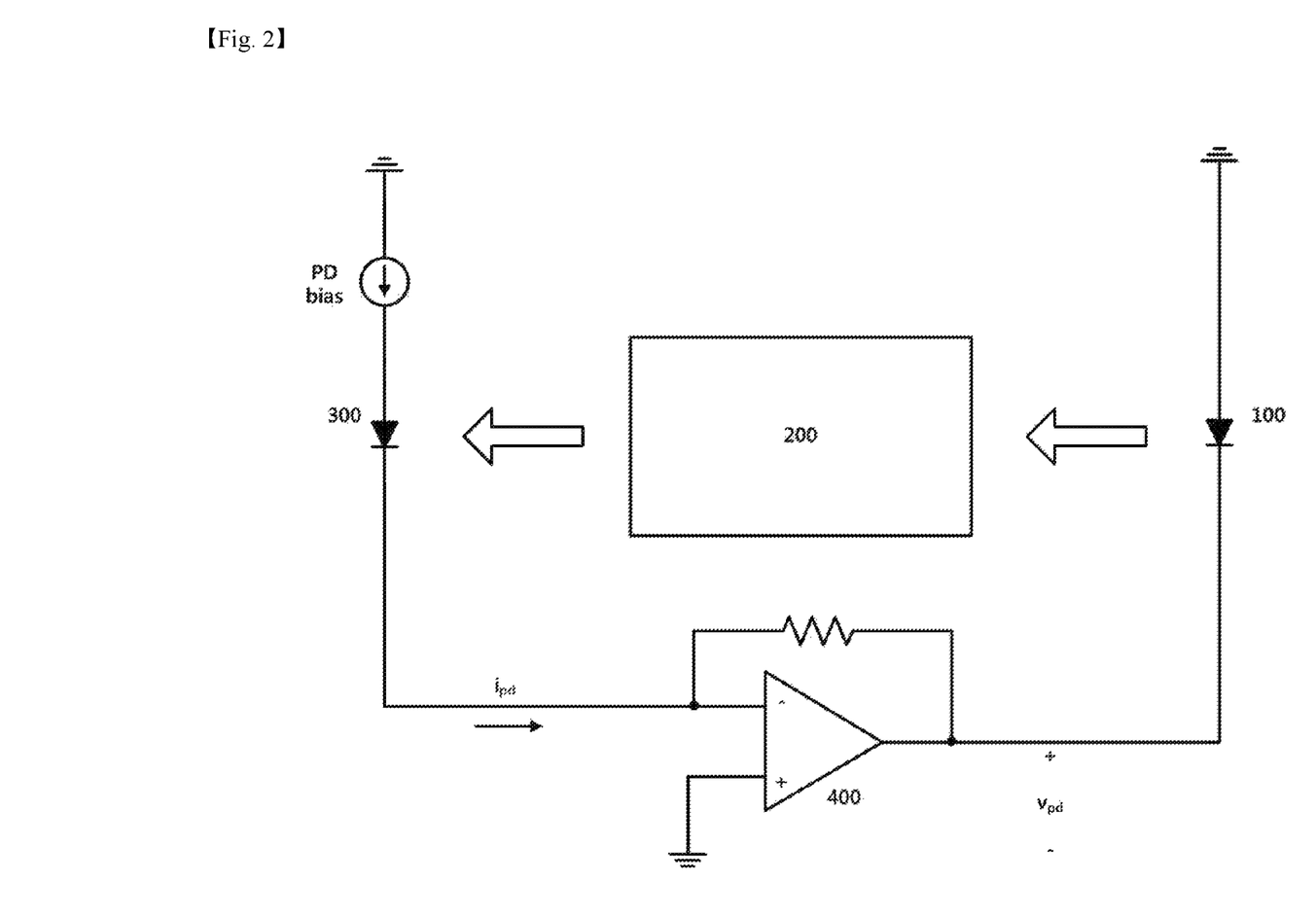
FIG. 2 illustrates a circuit diagram of the sensing system according to an embodiment of the present invention.

Hereinafter, embodiments of the present invention will be described with reference to the accompanying drawings. FIG. 1 illustrates a schematic block diagram of a sensing system according to an embodiment of the present invention, and FIG. 2 shows a circuit diagram of the sensing system according to the embodiment of the present invention. Referring to FIGS. 1 and 2, the sensing system according to the embodiment of the present invention includes an optical actuator 100. The optical actuator 100, in response to a bias applied thereto, applies an optical stimulus into a medium 200 that contains a detection target substance. Hereinafter, an actuator providing ultraviolet light, visible light, infrared light, and laser light is defined as an optical actuator, and an actuator applying a non-optical stimulus such as a sonic wave, a supersonic wave, a magnetic field, an electric field, and radioactivity is defined as a non-optical actuator. For example, an optical actuator may be implemented by an LED, a laser diode (LD) and the like, which provide light, in response to a bias applied thereto.

The LED may irradiate light having a wavelength band of visible light, ultraviolet light, or infrared light, and the LD may irradiate laser light having a predetermined band among 270 nm to 3330 nm. It may be preferable to configure the optical actuator capable of irradiating light of an appropriate band according to the property of a target substance to be detected by the sensing system.

The medium 200 includes a detection target substance to be detected by the sensing system according to the present embodiment. In response to an optical stimulus applied from the optical actuator 100, the detection target substance generates an optical response. The optical response generated by the detection target substance, with respect to the optical stimulus, for example, may be light through which light generated by the optical stimulus is transmitted through the medium, and light reflected from or scattered by the medium 200, or may be fluorescence produced by the optical stimulus. For instance, as an optical response, BSA has the property that absorbs light of 270 to 280 nm. Therefore, when irradiating a medium containing BSA with a laser light having a wavelength of 275 nm, BSA generates an optical response, in response to an optical stimulus applied thereto, by absorbing the laser light. This is, however, a description of an example, so it should be understood that an optical response may be different regarding to a detection target substance, an optical stimulus applied to the detection target substance, and an optical stimulus that is generated according to the detection target substance.

A photo detector 300 is configured to detect an optical response that is generated in response to an optical stimulus applied to the medium 200, and to output an electrical signal. For example, the photo detector 300 may be configured to output an electrical signal by detecting one or more among light which is generated by a detection target substance in response to an optical stimulus applied from the optical actuator 100 to be transmitted through the medium 200, light reflected from or scattered by the medium 200, and fluorescence produced by the medium 200 in response to an optical stimulus. Depending on the concentration of a detection target substance contained in the medium 200, an optical response may be varied such that an electrical signal provided from the photo detector 300 may be also changed. For example, the photo detector 300 may be configured with a photo diode, and the photo diode may detect a variation of light due to an optical response generated by the medium 200 to provide an electrical signal corresponding to the variation of light.

As one embodiment, the photo detector 300 may receive a driving current $i_{pd}$ from a power source PD bias providing a bias current, the sensing system according to the present embodiment may detect an optical response from the medium 200 by sweeping the driving current provided from the power source PD bias. As described below, the photo detector 300 outputs an electrical signal having a snapback form as the driving current is changed.

An amplifier 400 amplifies and outputs the electrical signal provided from the photo detector 300, and the amplified electrical signal is added to a bias from the actuator 100 to be provided thereto as a feedback. Thus, the actuator 100, the medium 200, the photo detector 300, and the amplifier 400 form a positive feedback path. For example, the amplifier 400 may be implemented with a current-voltage converter (i-v converter) for converting a current from the photo diode into a voltage signal, and an output voltage of the current-voltage converter circuit is positively fed back along with a bias (ACT bias) of the optical actuator 100.

As shown in FIG. 2, the current $i_{pd}$ provided from the photo detector 300 is converted into a voltage signal $v_{fb}$ by the amplifier 400. Since the voltage signal $v_{fb}$ has a negative potential, in comparison with a potential of one end of the optical actuator 100 connected to a reference potential, a potential of the other end thereof connected to the amplifier 400 is lower than that of the one end. Therefore, because a bias applied to the optical actuator 100 is increased as the voltage $v_{fb}$ of the amplifier 400 is increased so that an increased optical stimulus is applied, the medium 200 optically responses to the increased optical stimulus applied thereto, such that the photo detector 300 detects an optical response to provide an increased current $i_{pd}$. That is, the sensing system according to the present embodiment is configured with a positive feedback path.

A detection unit 500 receives and analyzes the electrical signal output from the photo detector 300 to detect a concentration of the detection target substance contained in the medium 200. For example, the detection unit 500 is provided with a read-out circuit to analyze an electrical signal OUTPUT from the photo detector 300 and detect the concentration of the detection target substance.

Figure 3:
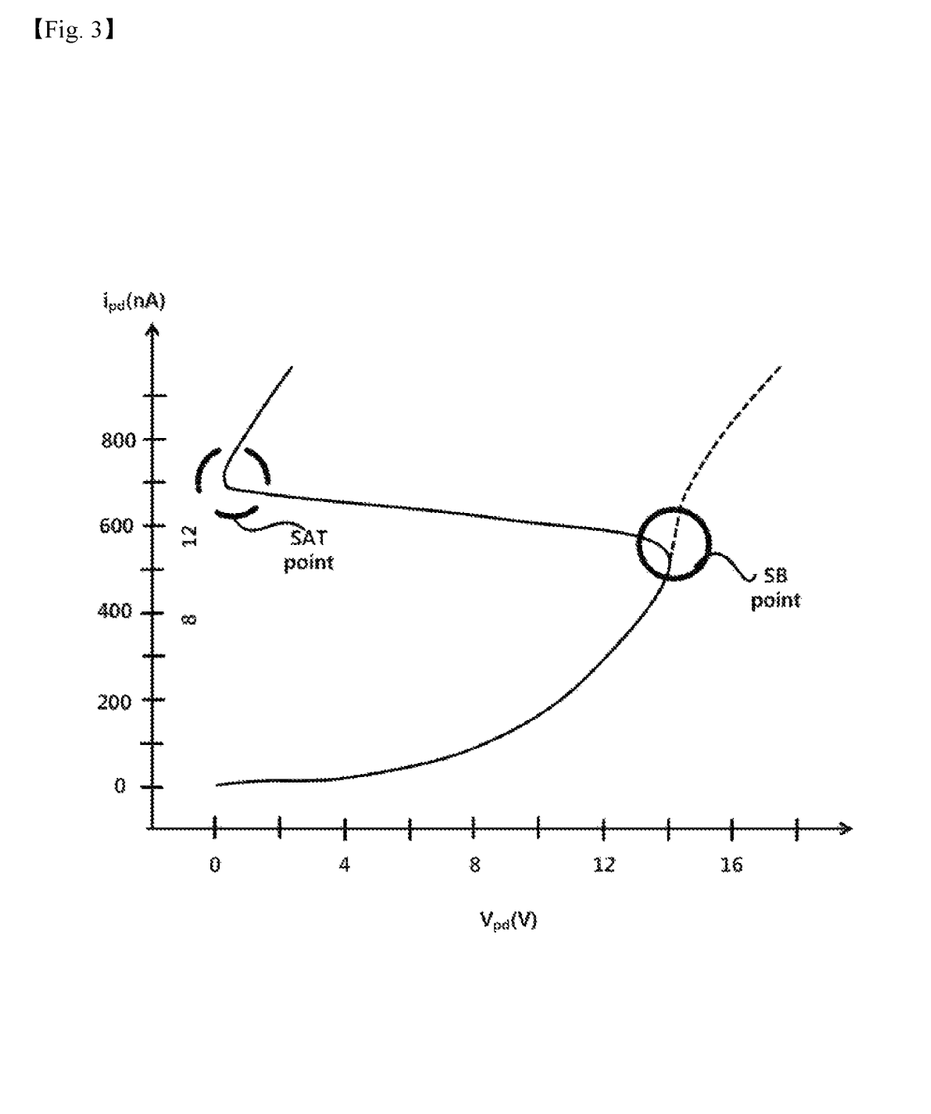
FIG. 3 illustrates a current-voltage characteristic curve of an electrical signal output from a photo detector when the sensing system according to an embodiment of the present invention detects a bovine serum albumin (BSA) as a detection target substance.

FIG. 3 illustrates a current-voltage characteristic curve of the electrical signal output from the photo detector 300 when the sensing system according to the present embodiment detects BSA as the detection target substance. In FIG. 3, a vertical axis represents a value of the bias current $i_{pd}$ applied to the photo detector 300 shown in FIGS. 1 and 2, and a horizontal axis represents a value of the voltage $v_{pd}$ across both ends of the photo detector 300.

With reference to FIGS. 1 to 3, a change of the voltage across the photo detector 300 while increasing the bias current from zero provided thereto will be described. As the bias current $i_{pd}$ provided to the photo detector 300 is increased, the voltage $v_{pd}$ across both ends of the photo detector 300 is correspondingly increased according to the increase of the bias current $i_{pd}$, but the optical actuator 100 is not yet turned on.

As the bias current $i_{pd}$ applied to the photo detector 300 is increased, the amplifier 400 applies a voltage higher than a turn-on voltage to the optical actuator 100, such that the optical actuator 100 is turned on. The optical actuator 100 turned on applies an optical stimulus into the medium 200, and when the medium 200 provides light as an optical response, the photo detector 300 detects the light from the medium 200 and converts the detected light into a corresponding current to output the current. At the time of the optical actuator 100 turned on, in order for the photo detector 300 to provide a constant current, the voltage across both ends of the photo detector 300 may be reduced so as to compensate for a current converted from the light provided by the medium 200 due to the optical response thereof. Therefore, the voltage is progressively decreased. That is, while the current provided from the power source to photo detector 300 is increased, the voltage across both ends of the photo detector 300 is decreased to have a negative resistance characteristic.

As described above, a phenomenon of which a voltage across both ends of the photo detector 300 is decreased while increasing a current applied thereto is called a snapback phenomenon, a starting point at which the snapback phenomenon occurs is called a snapback point (SB point), and a region of which a voltage is decreased due to the snapback phenomenon in spite of increasing a current is called a snapback region.

As the bias current of the photo detector 300 is further increased, the voltage across both ends of the photo detector 300 is decreased close to zero. At this time, this point is called a saturation point, and a region after the saturation point is called a saturation region.

Since the photo detector 300 decreases the voltage across both ends thereof in order to compensate for a corresponding current according to the increased light provided from the medium 200, when the medium 200 provides more light to the photo detector 300 in response to more optical stimulus due to the positive feedback as the bias current of the photo detector 300 is increased, such that the saturation occurs, the voltage across both ends of the photo detector 300 is constantly maintained near the saturation region as the bias current is continually increased so that there is almost no change in the voltage in spite of increasing the current. However, as shown in FIG. 3, the voltage may be increased as much as several volts, but, with reference to FIG. 4 illustrating the voltage of both ends of the photo detector 300 in a 100 volt scale, a voltage change with respect to a current change in the saturation region is very insignificant.

Furthermore, a dotted line of the curve in FIG. 3 represents a current-voltage characteristic obtained when a signal path is configured with an open loop without a positive feedback path. In comparison with the dotted line of the curve, it is understood that the snapback characteristic may be realized by connecting the optical actuator 100, the medium 200, the photo detector 300, and the amplifier 400 in a positive feedback manner.

Figure 4:
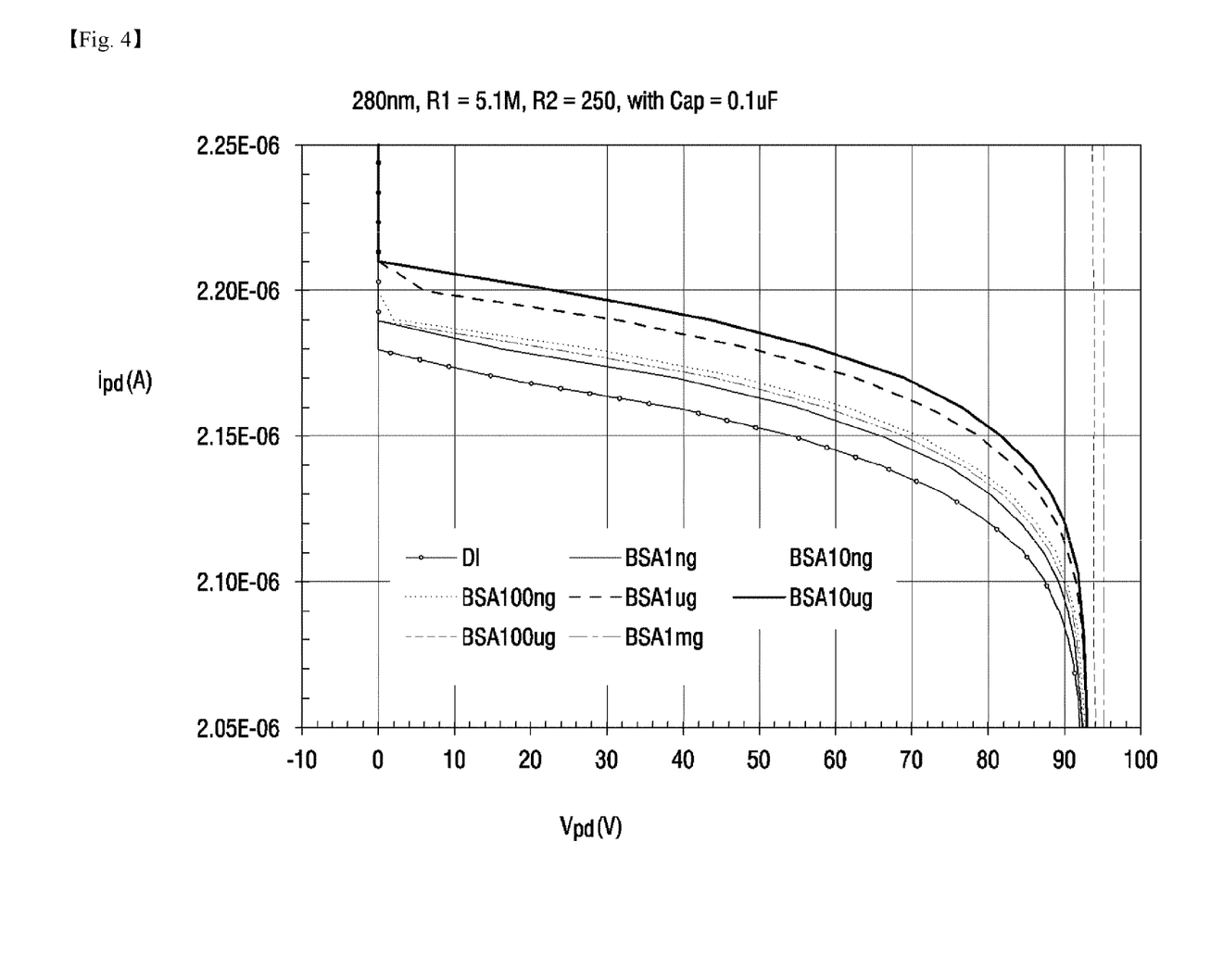
FIG. 4 illustrates a measurement result for a current-voltage characteristic of the detection target substance according to the change of concentration in a snapback region.

FIG. 4 illustrates a measurement result for a current-voltage characteristic of the detection target substance according to the change of concentration in a snapback region, and, more particularly, a current-voltage curve obtained by detection by using the sensing system according to the present embodiment for the medium 200 in which a detection target substance of BSA in the amounts of 1 nanogram (ng), 10 ng, . . . , 1 milligram (mg), respectively, are added to deionized water. As shown in FIG. 4, when a current of about 2.1 microamperes (μA) to 2.15 uA is applied to the photo detector 300, the snapback phenomenon occurs, and then a voltage is saturated to about zero volts at 2.17 μA to 2.21 μA.

According to the concentration of the detection target substance, the current-voltage characteristic is changed in the snapback region. Therefore, the detection unit 500 may readout a voltage across both ends of the photo detector 300 by constantly maintaining a bias current thereof, or readout a bias current of the photo detector 300 by constantly maintaining a voltage of both ends thereof, thereby detecting the concentration of the detection target substance. For example, when a bias current of the photo detector 300 is constantly maintained at 2.15 μA, the detection unit 500 readouts 66 volts as a voltage across both ends of the photo detector 300 to detect a concentration of the detection target substance as 1 ng. As another example, when a voltage across both ends of the photo detector 300 is constantly maintained at 40 volts, the detection unit 500 readouts 2.18 μA as a bias current of the photo detector 300 to detect a concentration of the detection target substance as 100 ng. Furthermore, the concentration of the detection target substance may be detected by measuring a current and/or a voltage at the saturation point beyond the snapback region.

Hereinafter, an implementation of the sensing system according to the embodiment of the present invention and a detection result of the detection target substance by using the implementation will be described. FIG. 2 illustrates a circuit diagram of an implementation of the sensing system according to the present embodiment, the power source for applying a bias current to the photo detector 300 is a Model 4156 of Agilent Technologies, the photo detector 300 is a UV (Ultraviolet) enhanced silicon photodiode (Model 100-13-23-222) of Advanced Photonix, Inc., and an operation amplifier 400 is an operational amplifier (Model OPA544) of Burr-Brown Corp. used for high-voltage/high-current. A feedback resistance included in the operational amplifier 400 is 6.1 megaohms (Mohm). The optical actuator 100 is an LED capable of irradiating lights of various wavelengths according to types of detection target substances to be measured.

Figure 5A:
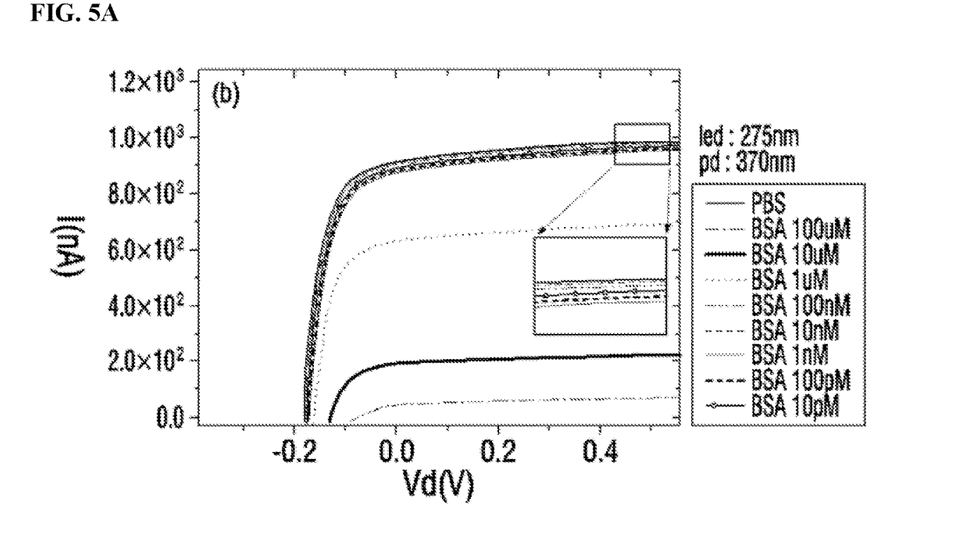
FIG. 5a illustrates the measurement result of BSA measured by using a sensor according to the prior art.
Figure 5B:
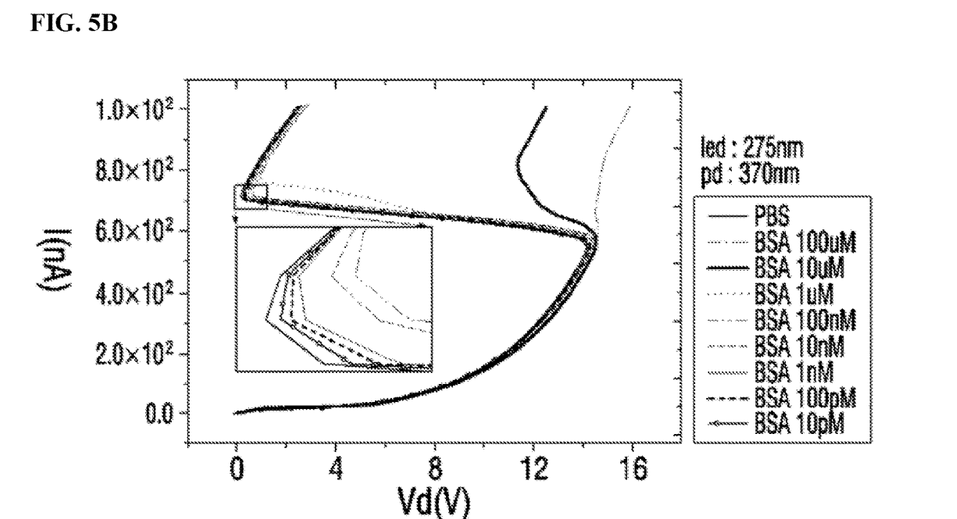
FIG. 5b illustrates the measurement result of BSA measured by the present embodiment.
Figure 5C:
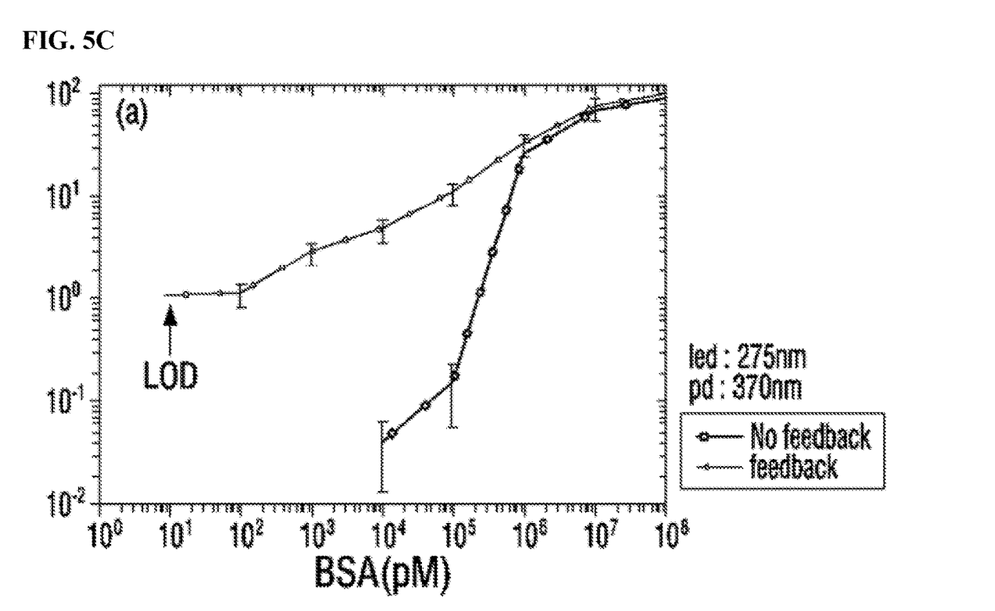
FIG. 5c illustrates a BSA detection capability of a sensing system according to the present embodiment.

In order to test a detection possibility of protein contained in water, BSA having different concentrations in the range of 10 picomoles (pM) to 100 micromoles (μM) was measured. The measurement result of a sensor according to the prior art is shown in FIG. 5a, and that of the present embodiment is shown in FIG. 5b. As described above, it can be seen that the snapback phenomenon due to the positive feedback has occurred. Based on the measurement result, the detection capability of BSA is shown in FIG. 5c. As shown in FIG. 5c, the sensing system of the present embodiment is capable of measuring the BSA protein having a concentration in the range of 10 to $10^3$ pM which is very difficult to measure though the sensor according to the prior art.

In order to detect the existence of a water microorganism, a concentration of NADH is measured. NAD (nicotinamide-adenine-dinucleotide) is an important coenzyme that is found in a cell, and NADH is the reduced form of NAD and is generated during a cellular metabolic process according to a reaction formula described below.

Figure 6A:
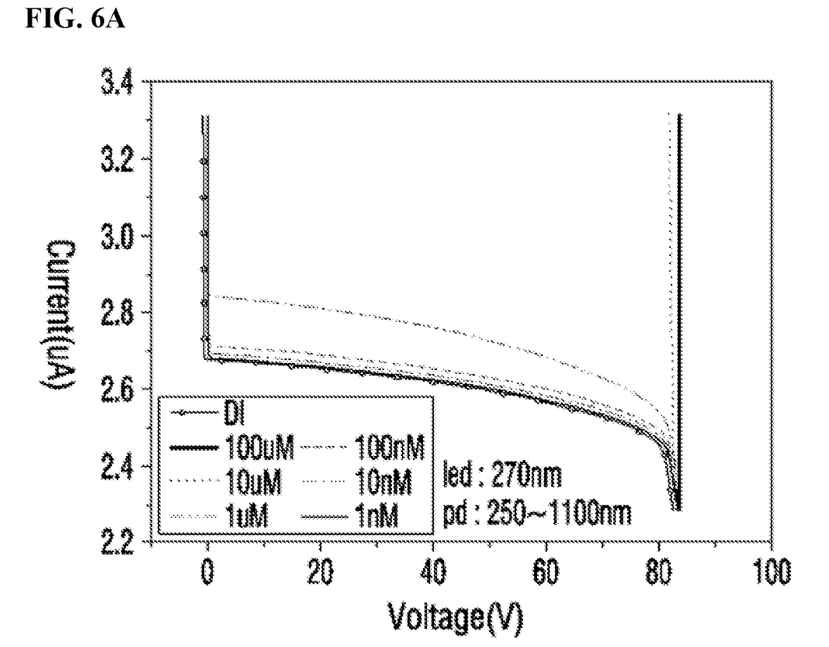
FIGS. 6a to 6c illustrate current-voltage characteristic curves of NADH (nicotinamide-adenine-dinucleotide hydrogenase) measured by using each of 270 nanometer (nm), 280 nm, and 340 nm light emitting diodes (LEDs).
Figure 6B:
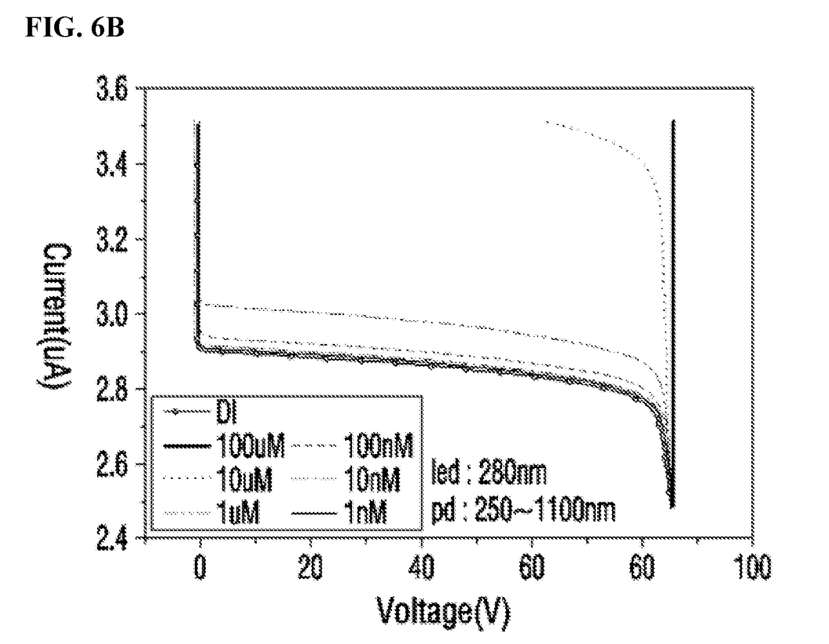
Figure 6C:
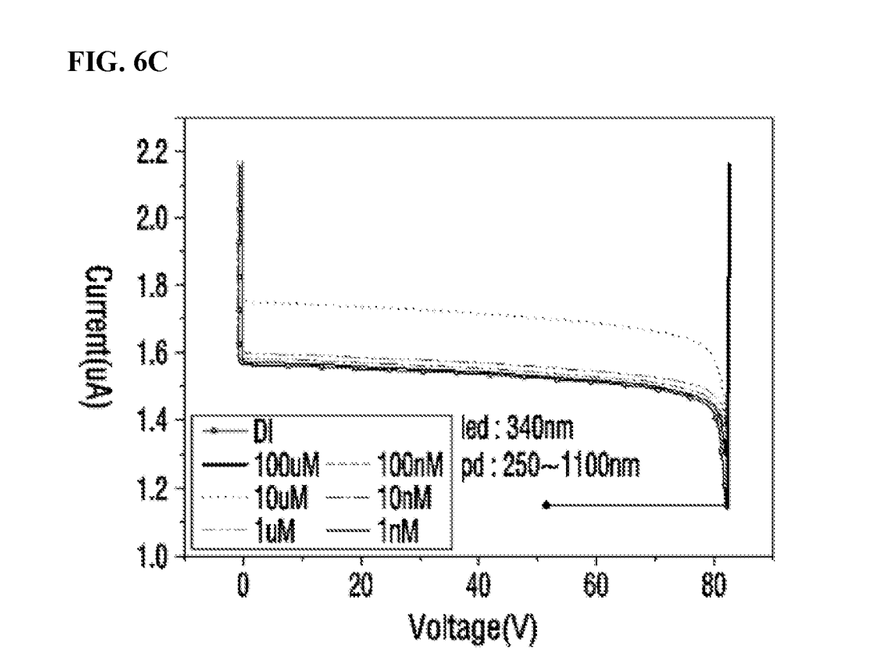
Figure 6D:
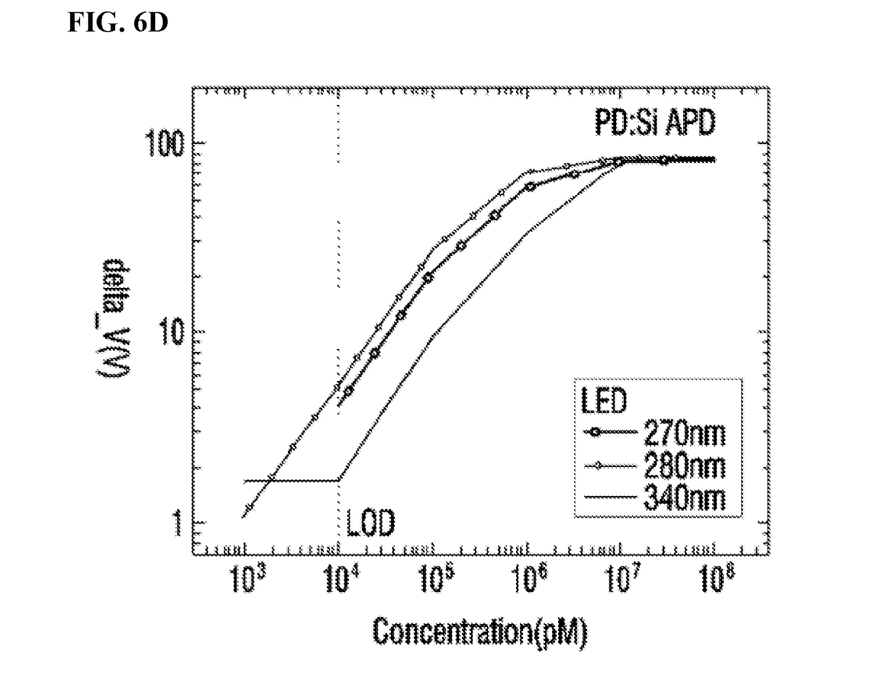
FIG. 6d illustrates an NADH measurement capability of the sensing system according to the present embodiment.

Therefore, by measuring the existence of NADH, it is found whether or not the microorganism exists in water. Since a nucleotide is the basic framework of NADH, a wavelength of maximum absorption of NADH is 260 nm which is the same as that of deoxyribonucleic acid (DNA). Because a wavelength of 340 nm is easily absorbed by NADH, it is possible to measure the activity of a dehydration coenzyme by using an LED having a wavelength of 340 nm. In this experimental example, NADH is measured by using LEDs having wavelengths of 270 nm, 280 nm, and 340 nm, respectively, and current-voltage characteristics are shown in FIGS. 6a to 6c. Also, based on the measurement results, the NADH measurement capability is shown in FIG. 6d. As shown in FIG. 6d, it can be confirmed that it is possible to measure NADH having a concentration near 10 nM by using the sensing system according to the present embodiment.

Figure 7:
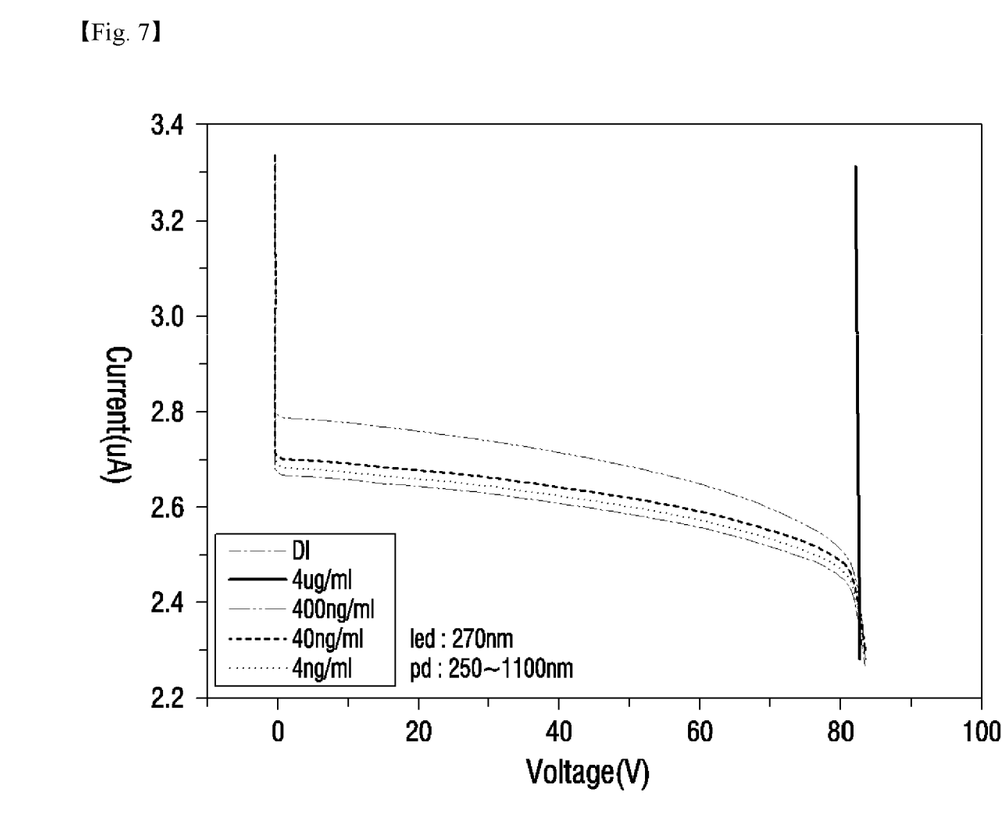
FIG. 7 illustrates a current-voltage characteristic curve with respect to the concentration measurement result of a graphene oxide.

Referring to FIG. 7, there is shown a current-voltage characteristic curve with respect to the measurement result of concentration of a graphene oxide that is one of toxic substances in aquatic environments. As seen from FIG. 7, it is possible to detect a concentration near 4 ng/ml (milliliter), but a spectrometer according to the prior art may measure a concentration of several ug/ml such that it can be determined that the measurement ability of the sensing system according to the present embodiment is superior to that of the conventional sensor.

Figure 8A:
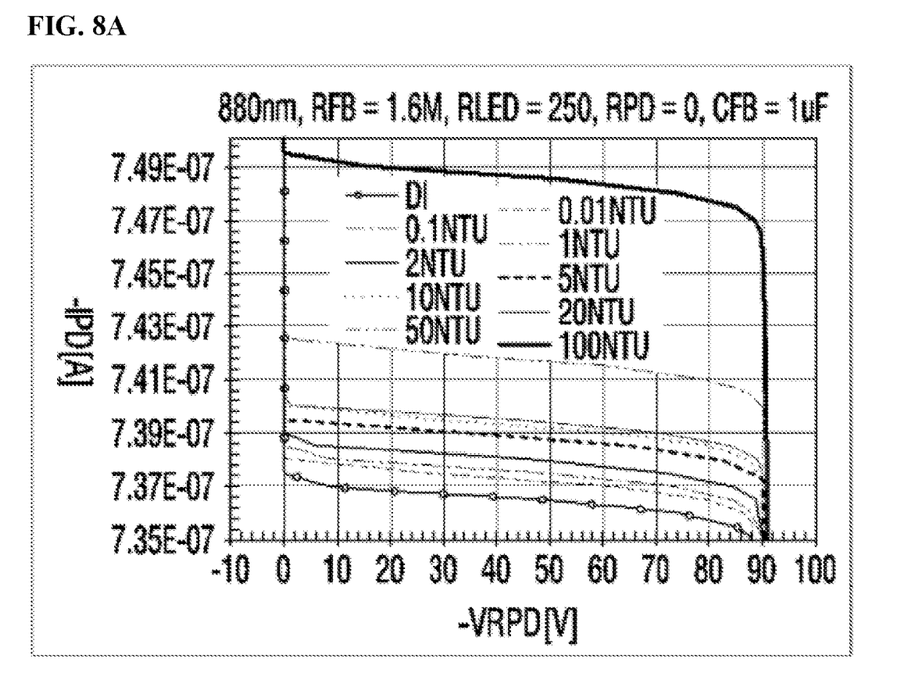
FIGS. 8a to 8c illustrate current-voltage curves with respect to a turbidity measurement result by using each of 880 nm, 405 nm, 280 nm infrared (IR) LEDs.
Figure 8B:
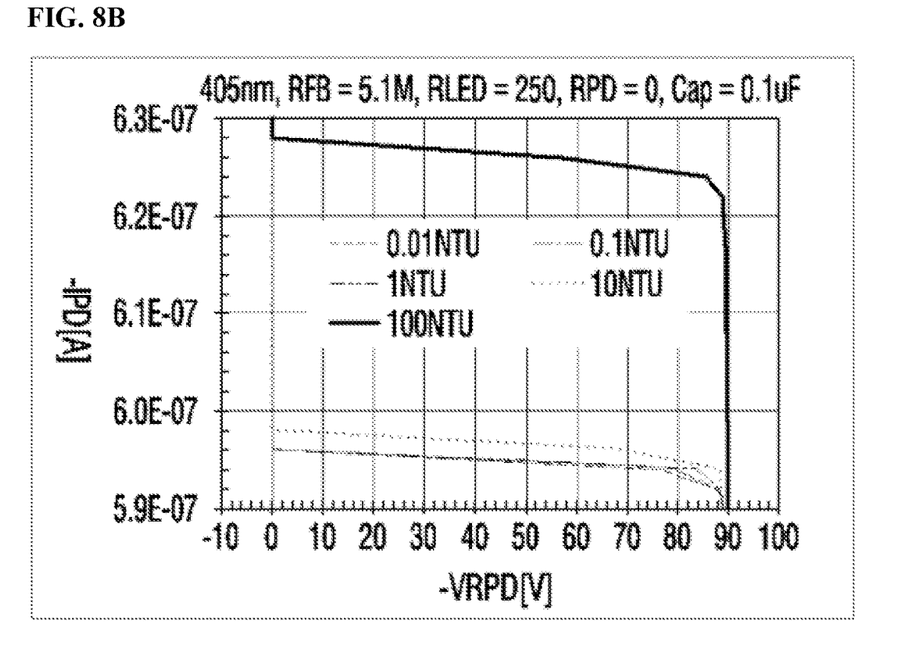
Figure 8C:
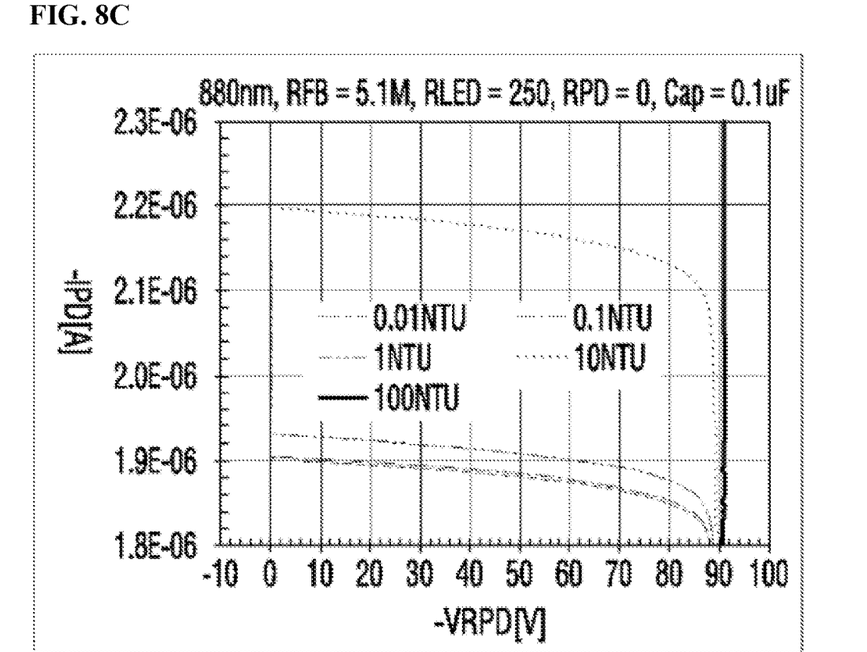
Figure 8D:
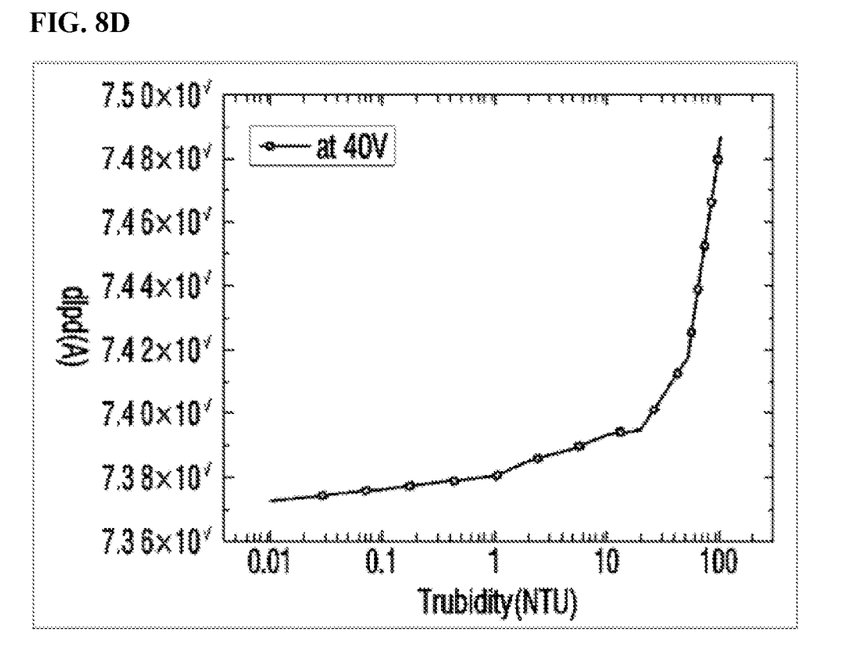
FIG. 8d illustrates the LOD (limit of detection) of the sensing system according to the present embodiment.

In order to verify a measurement capability for detecting floating matter in water, turbidity is measured by using infrared LEDs with wavelengths of 880 nm, 405 nm, and 280 nm. FIGS. 8a to 8c illustrate an expanded snapback region with respect to each wavelength, and FIG. 8d illustrates the LOD of the sensing system according to the embodiment of the present invention. As shown in FIG. 8a, it is possible to accurately measure a very low concentration around an 880 nm wavelength. Considering the LOD based on the above measurement result, as shown in FIG. 8d, it is possible to detect a concentration near 0.01 nephelometric turbidity units (NTU).

While the foregoing invention has been described with reference to the above-described embodiment, various modifications and changes can be made without departing from the spirit of the invention. Accordingly, all such modifications and changes are considered to be within the scope of the appended claims. Accordingly, the specification and the drawings are to be regarded in an illustrative rather than a restrictive sense. The accompanying drawings that form a part herein, show by way of illustration, and not of limitation, specific embodiments by which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This detailed description, therefore, is not to be taken in a limiting sense, and the scope of various embodiments is defined only by the appended claims, along with the full range of equivalents to which such claims are entitled.

REFERENCE NUMERALS

100: optical actuator
200: medium containing detection target substance
300: photo detector
400: amplifier
500: detection unit

The invention claimed is:

1. A sensing system, comprising:
   an optical actuator configured to apply an optical stimulus into a detection target substance;
   a photo detector configured to output an electrical signal having a snapback form in response to an optical response generated according to a concentration of the detection target substance to which the optical stimulus is applied;
   an amplifier configured to amplify the electrical signal output from the photo detector and to provide the amplified electrical signal as positive feedback to the optical actuator; and
   a detection unit configured to detect the detection target substance in response to the electrical signal,
   wherein the optical actuator includes one of a light emitting diode (LED) and a laser diode (LD).

2. The sensing system of claim 1, further comprising:
   a power source configured to apply a bias current to the photo detector.

3. The sensing system of claim 1, wherein the photo detector includes a photodiode.

4. The sensing system of claim 1, wherein the photo detector is configured to detect one or more among reflected light, transmitted light, scattered light, and fluorescence, each of which is generated by the detection target substance in response to the optical stimulus applied from the optical actuator, thereby outputting the electrical signal corresponding to the detection result.

5. The sensing system of claim 1, wherein the amplifier is a current-voltage conversion amplifier which receives a current signal, converts the current signal into a corresponding voltage signal and outputs the converted voltage signal.

6. The sensing system of claim 1, wherein the electrical signal having a snapback form includes a snapback region in which the electrical signal is decreased as a voltage across both ends of the photo detector is increased from a snapback point, and a saturation region in which the electrical signal is increased as the voltage across both ends of the photo detector is increased, wherein the snapback region and the saturation region are connected through a saturation point.

7. The sensing system of claim 6, wherein the detection unit detects a concentration of the detection target substance by detecting the voltage across both ends of the photo detector when a constant current is provided to the photo detector in the snapback region.

8. The sensing system of claim 6, wherein the detection unit detects a concentration of the detection target substance by detecting a current flowing to the photo detector when a constant voltage is provided to the photo detector in the snapback region.

9. The sensing system of claim 6, wherein the detection unit detects a concentration of the detection target substance by detecting current and voltage values at the saturation point.

10. The sensing system of claim 6, wherein the detection unit detects a concentration of the detection target substance by detecting a current-to-voltage ratio of the saturation region.

11. A sensing system, comprising:
    an optical actuator configured to apply an optical stimulus into a detection target substance;
    a photo detector configured to receive a bias current and an incident light generated by an optical response of the detection target substance; and
    a positive feedback unit configured to increase the optical stimulus applied from the optical actuator as the bias current increases, wherein the optical actuator includes at least one of an LED and an LD, and the photo detector includes a photodiode.

12. The sensing system of claim 11, wherein the positive feedback unit increases a forward voltage of the diode included in the optical actuator as the bias current increases.

13. The sensing system of claim 11, wherein the positive feedback unit includes a differential amplifier,
wherein a reference voltage is applied to a first input end of the differential amplifier, the bias current is provided to a second input end of the differential amplifier, a resistor is connected between the second input end and an output end of the differential amplifier, and the output end is connected to the diode included in the optical actuator.

14. The sensing system of claim 11, wherein the photo detector outputs a sensing voltage corresponding to the bias current and the incident light.

15. The sensing system of claim 14, wherein the photo detector includes a snapback region in which the sensing voltage is decreased as the bias current increases.

16. The sensing system of claim 15, further comprising:
a detection unit configured to measure a concentration of the detection target substance by measuring the sensing voltage while supplying a predetermined amount of the bias current in the snapback region.

17. The sensing system of claim 11, wherein the incident light includes at least one among reflected light, transmitted light, scattered light, and fluorescence which are formed by applying the optical stimulus into the detection target substance.

18. The sensing system of claim 11, wherein the detection target substance includes at least one among BSA (bovine serum albumin), NADH (chemically reduced form of NAD (nicotinamide-adenine-dinucleotide)), a graphene oxide, and floating matter.

* * * * *